US00PP30928P3

(12) United States Plant Patent
Koot

(10) Patent No.: US PP30,928 P3
(45) Date of Patent: Oct. 8, 2019

(54) ***VERBENA* PLANT NAMED 'DOVEMSULC'**

(50) Latin Name: ***Verbena* X *hybrida***
Varietal Denomination: Dovemsulc

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,833

(22) Filed: Jan. 3, 2018

(65) Prior Publication Data

US 2019/0208687 P1 Jul. 4, 2019

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
See application file for complete search history.

(56) References Cited

PUBLICATIONS https://cdn.shopify.com/s/files/1/1537/5553/files/mast.pdf (Retrieved from the Internet on Dec. 15, 2018). 2 pages total.*
http://trialgardenspsu.com/summary.php?menu (Retrieved from the Internet on Dec. 17, 2018). 2 pages total.*

* cited by examiner

*Primary Examiner* — Susan McCormick Ewoldt
(74) *Attorney, Agent, or Firm* — C. A. Whealy

(57) ABSTRACT

A new and distinct cultivar of *Verbena* plant named 'Dovemsulc', characterized by its semi-trailing and mounding plant habit; vigorous growth habit; freely branching habit; early and freely flowering habit; and large violet and white bi-colored flowers that are held above and beyond the foliar plane in mounded umbels.

1 Drawing Sheet

Botanical designation: *Verbena* X *hybrida*.
Cultivar denomination: 'DOVEMSULC'.

BACKGROUND OF THE INVENTION

The present invention relates to a new and distinct cultivar of *Verbena* plant, botanically known as *Verbena* X *hybrida* and hereinafter referred to by the name 'Dovemsulc'.

The new *Verbena* plant is a product of a planned breeding program conducted by the Inventor in Rheinberg, Germany. The objective of the breeding program is to create new vigorous and early-flowering *Verbena* plants with numerous large and attractive flowers.

The new *Verbena* plant originated from a cross-pollination made by the Inventor in July, 2014 in Rheinberg, Germany of a proprietary selection of *Verbena* X *hybrida* identified as code number VV12-003831-005, not patented, as the female, or seed, parent with a proprietary selection of *Verbena* X *hybrida* identified as code number VV-0341, not patented, as the male, or pollen, parent. The new *Verbena* plant was discovered and selected by the Inventor as a single flowering plant within the progeny of the stated cross-pollination in a controlled greenhouse environment in Rheinberg, Germany in May, 2017.

Asexual reproduction of the new *Verbena* plant by terminal vegetative cuttings in a controlled greenhouse environment in Rheinberg, Germany since June, 2017 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dovemsulc'. These characteristics in combination distinguish 'Dovemsulc' as a new and distinct *Verbena* plant:

1. Semi-trailing and mounding plant habit.
2. Vigorous growth habit.
3. Freely branching habit.
4. Early and freely flowering habit.
5. Large violet and white bi-colored flowers; flowers held above and beyond the foliar plane in mounded umbels.

Plants of the new *Verbena* differ primarily from plants of the female parent selection in the following characteristics:

1. Plants of the new *Verbena* are more vigorous than plants of the female parent selection.
2. Plants of the new *Verbena* flower earlier than plants of the female parent selection.

Plants of the new *Verbena* differ primarily from plants of the male parent selection in the following characteristics:

1. Plants of the new *Verbena* are more vigorous than plants of the male parent selection.
2. Plants of the new *Verbena* have larger flowers than plants of the male parent selection.
3. Plants of the new *Verbena* and the male parent selection differ in flower color as plants of the male parent selection have red-colored flowers.

Plants of the new *Verbena* can be compared to plants of the *Verbena* sp. 'KLEVP15498', disclosed in U.S. Plant Pat.

No. 26,958. In side-by-side comparisons, plants of the new *Verbena* differ primarily from plants of 'KLEVP15498' in the following characteristics:

1. Plants of the new *Verbena* are more vigorous than plants of 'KLEVP15498'.
2. Plants of the new *Verbena* have thicker stems than plants of 'KLEVP15498'.
3. Plants of the new *Verbena* have longer leaves than plants of 'KLEVP15498'.
4. Plants of the new *Verbena* have larger flowers than plants of 'KLEVP15498'.
5. Plants of the new *Verbena* and 'KLEVP15498' differ in flower color as plants of 'KLEVP15498' have dark purple and white bi-colored flowers.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the colors of the new *Verbena* plant. The photograph is a side perspective view of a typical flowering plant of 'Dovemsulc'.

DETAILED BOTANICAL DESCRIPTION

The aforementioned photograph and following observations, measurements and values describe plants grown in 22-cm containers during the spring and summer in a glass-covered greenhouse in Rheinberg, Germany and under cultural practices typical of commercial *Verbena* production. During the production of the plants, day and night temperatures averaged 18° C. and light levels averaged 4,500 lux. Plants were pinched one time three weeks after planting and were ten weeks old when the photograph and the description were taken. In the description, color references are made to The Royal Horticultural Society Colour Chart, 2007 Edition, except where general terms of ordinary dictionary significance are used.

Botanical classification: *Verbena* X hybrida 'Dovemsulc'.

Parentage:

*Female, or seed, parent*.—Proprietary selection of *Verbena* X *hybrida* identified as code number VV12-003831-005, not patented.

*Male, or pollen, parent*.—Proprietary selection of *Verbena* X *hybrida* identified as code number VV-0341, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant habit*.—Semi-trailing and mounding plant habit; freely branching habit with about six primary lateral branches each with about 12 to 14 secondary lateral branches; pinching enhances lateral branch development; dense and bushy plant habit; vigorous growth habit.

*Plant height, soil level to top of foliar plane*.—About 27 cm.

*Plant height, soil level to top of floral plane*.—About 29 cm.

*Plant diameter*.—About 82 cm.

Lateral branch description:

*Length*.—About 51 cm.

*Diameter*.—About 6 mm.

*Internode length*.—About 2 cm.

*Strength*.—Strong.

*Texture and luster*.—Pubescent; semi-glossy.

*Color, developing*.—Close to 144B; at the internodes, close to 137C.

*Color, developed*.—Close to 137C; at the internodes, close to 137C.

Leaf description:

*Arrangement*.—Opposite, simple.

*Length*.—About 3.7 cm.

*Width*.—About 1.7 cm.

*Shape*.—Lanceolate.

*Apex*.—Acute.

*Base*.—Attenuate.

*Margin*.—Lobed.

*Texture and luster, upper surface*.—Pubescent, coarse; semi-glossy.

*Texture and luster, lower surface*.—Pubescent, coarse; matte.

*Venation pattern*.—Pinnate.

*Color*.—Developing leaves, upper surface: Close to N137B. Developing leaves, lower surface: Close to 147B. Fully expanded leaves, upper surface: Close to N137B; venation, close to 147A. Fully expanded leaves, lower surface: Close to 147B; venation, close to 147C.

*Petioles*.—Length: About 2 mm. Diameter: About 1.1 mm. Strength: Moderately strong. Texture and luster, upper and lower surfaces: Smooth, glabrous; matte. Color, upper and lower surfaces: Close to 147D.

Flower description:

*Flower arrangement and habit*.—Salverform flowers arranged in hemispherical terminal umbels; umbels dense and mounding; numerous umbels per plant; flowers face upward or outwardly depending on position in the umbel; freely flowering habit with about 12 to 15 flowers per inflorescence and about 250 to 500 flowers developing per plant.

*Fragrance*.—None detected.

*Natural flowering season*.—Plants flower continuously from the spring through the fall in Northern Europe; plants begin flowering about eight weeks after planting.

*Flower longevity*.—Individual flowers last about one week on the plant; flowers persistent.

*Inflorescence height*.—About 3.3 cm.

*Inflorescence diameter*.—About 6 cm.

*Flower buds*.—Length: About 1.5 cm. Diameter: About 3 mm. Shape: Oval to tubular. Texture and luster: Rippled; matte. Color: Close to N80D and 145B.

*Flowers*.—Appearance: Salverform, five-parted fused corolla. Diameter: About 1.8 cm. Depth: About 3 cm. Throat diameter: About 2 mm. Tube length: About 2.2 cm. Tube diameter: About 1.8 mm.

*Corolla*.—Arrangement: Single whorl of five fused petals. Petal lobe length: About 9 mm. Petal lobe width: About 7 mm. Petal lobe shape: Obovate. Petal lobe apex: Emarginate. Petal margin: Entire. Petal texture and luster, upper and lower surfaces: Smooth, glabrous; matte. Throat texture and luster: Smooth, glabrous; matte. Tube texture and luster: Smooth, glabrous; matte. Color: Petal lobe, when opening, upper surface: Distally, close to N81A; towards the throat, close to NN155B. Petal lobe, when opening, lower surface: Distally, close to N81D; towards the throat, close to NN155B. Petal lobe, fully opened, upper surface: Distally, close to N87A; towards the throat, close to NN155B; venation, similar to lamina color; color fading to NN155B with development. Petal lobe, fully opened, lower surface: Distally, close to N87C; towards the throat, close to NN155B; venation, similar to lamina color; color fading to NN155B with development. Throat: Close to 145C; venation, close to 145C. Tube: Close to 145C; venation, close to 145C.

*Calyx*.—Arrangement: Star-shaped calyx with five fused sepals. Length: About 1.9 cm. Diameter: About 3.2 mm. Sepal length: About 1.9 cm. Sepal width: About 2 mm. Sepal shape: Ligulate. Sepal apex: Acute. Sepal margin: Entire. Sepal texture and luster, upper surface: Pubescent, coarse; semi-glossy. Sepal texture and luster, lower surface: Pubescent, coarse; matte. Sepal color, when developing, upper and lower surfaces: Close to 145B and 144A. Sepal color, fully developed, upper and lower surfaces: Close to 145B and 144A.

*Peduncles*.—Length: About 4.5 cm. Diameter: About 2 mm. Strength: Strong. Aspect: Mostly upright. Texture and luster: Pubescent; semi-glossy. Color: Close to 144B.

*Pedicels*.—Length: About 1.5 mm. Diameter: About 0.5 mm. Strength: Strong. Aspect: Mostly upright. Texture and luster: Smooth, glabrous; semi-glossy. Color: Close to 144B.

*Reproductive organs*.—Stamens: Quantity and arrangement: About four per flower, adnate to corolla tube. Filament length: About 0.5 mm. Filament color: Close to 155C. Anther length: About 0.5 mm. Anther shape: Oval. Anther color: Close to 144C. Pollen amount: Moderate. Pollen color: Close to 2D. Pistils: Quantity: One per flower. Pistil length: About 1.9 cm. Style length: About 1.8 cm. Style color: Close to 142A. Stigma diameter: About 1 mm. Stigma shape: Bi-parted; fimbriate. Stigma color: Close to 147C. Ovary color: Close to 144A. Fruits: Quantity produced per plant: About 500 to 600 during the flowering season. Length: About 5 mm. Diameter: About 1 mm. Texture: Rough. Color: Close to 199C. Seeds: Quantity per flower: About four. Length: About 4.8 mm. Diameter: About 0.8 mm. Texture: Smooth, glabrous. Color: Close to 199B.

Temperature tolerance: Plants of the new *Verbena* have been observed to tolerate temperatures from about 11° C. to about 25° C.

Pathogen & pest resistance: Plants of the new *Verbena* have not been observed to be resistant to pathogens and pests common to *Verbena* plants to date.

It is claimed:

1. A new and distinct *Verbena* plant named 'Dovemsulc' as illustrated and described.

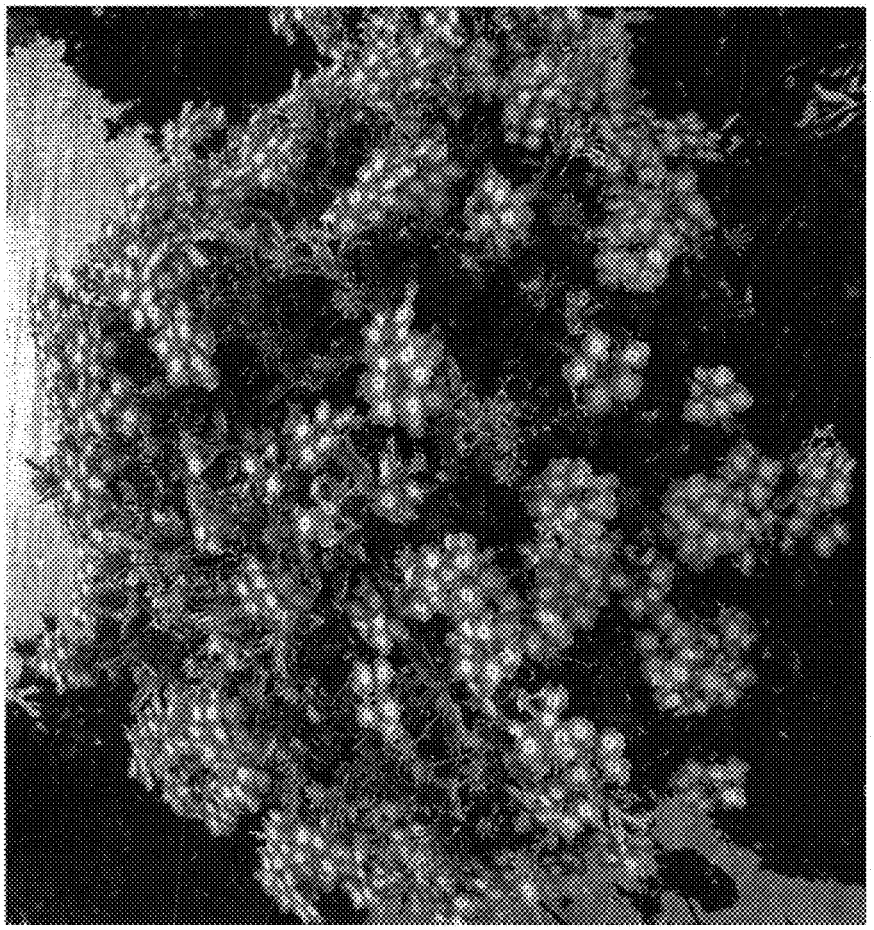

* * * * *